(12) United States Patent
Freeman et al.

(10) Patent No.: US 11,819,273 B2
(45) Date of Patent: Nov. 21, 2023

(54) AUGMENTED AND EXTENDED REALITY GLASSES FOR USE IN SURGERY VISUALIZATION AND TELESURGERY

(71) Applicant: Raytrx, LLC, Tulsa, OK (US)

(72) Inventors: Michael Hayes Freeman, Tulsa, OK (US); Mitchael C. Freeman, Sapulpa, OK (US); Jordan Boss, Tulsa, OK (US); Brian Santee, Tulsa, OK (US); David Cary, Tulsa, OK (US)

(73) Assignee: Raytrx, LLC, Tulsa, OK (US)

( * ) Notice: Subject to any disclaimer, the term of this patent is extended or adjusted under 35 U.S.C. 154(b) by 273 days.

(21) Appl. No.: 17/034,944

(22) Filed: Sep. 28, 2020

(65) Prior Publication Data

US 2021/0022599 A1    Jan. 28, 2021

Related U.S. Application Data

(63) Continuation-in-part of application No. 16/173,719, filed on Oct. 29, 2018, now Pat. No. 10,874,297,
(Continued)

(51) Int. Cl.
*A61B 3/00* (2006.01)
*A61B 3/12* (2006.01)
(Continued)

(52) U.S. Cl.
CPC .......... *A61B 3/0025* (2013.01); *A61B 3/024* (2013.01); *A61B 3/032* (2013.01); *A61B 3/12* (2013.01);
(Continued)

(58) Field of Classification Search
CPC .......... G06F 3/013; G06F 3/011; G06F 3/017; G06F 3/04815; G06F 3/012; G06F 1/163; G06F 3/0346; G06F 3/04842; G06F 3/147; G06F 3/0304; G06F 3/0481; G06F 3/14; G06F 3/1423; G06F 3/014; G06F 3/016;
(Continued)

(56) References Cited

U.S. PATENT DOCUMENTS 10,149,958 B1   12/2018   Tran et al.
2002/0082498 A1   6/2002   Wendt et al.
(Continued)

FOREIGN PATENT DOCUMENTS

KR   10-2014-0112207   9/2014

OTHER PUBLICATIONS

International Search Report and Written Opinion (International PCT Patent Application No. PCT/US2020/053098); dated Jan. 13, 2021.

*Primary Examiner* — Brandi N Thomas
(74) *Attorney, Agent, or Firm* — Head, Johnson, Kachigian & Wilkinson, PC

(57) ABSTRACT

An augmented reality and extended reality surgical system. The system may comprise a wearable device, such as a head mounted display or glasses, that provides the user with virtual reality, augmented reality, and/or mixed reality for surgery visualization. This may allow the user to access 2D or 3D imaging, magnification, virtual visualization, six-degrees of freedom (6DoF) image management, and/or other images while still viewing real reality and thus maintaining a presence in the operating room.

18 Claims, 9 Drawing Sheets

Related U.S. Application Data which is a continuation of application No. 15/940,561, filed on Mar. 29, 2018, now Pat. No. 10,111,583, which is a continuation of application No. 15/073,144, filed on Mar. 17, 2016, now Pat. No. 9,955,862, application No. 17/034,944 is a continuation-in-part of application No. 15/962,661, filed on Apr. 25, 2018, application No. 17/034,944 is a continuation-in-part of application No. 16/511,451, filed on Jul. 15, 2019, now Pat. No. 11,016,302, which is a continuation-in-part of application No. 16/511,202, filed on Jul. 15, 2019, now Pat. No. 11,461,936.

(60) Provisional application No. 62/907,300, filed on Sep. 27, 2019, provisional application No. 62/134,422, filed on Mar. 17, 2015, provisional application No. 62/489,801, filed on Apr. 25, 2017, provisional application No. 62/697,854, filed on Jul. 13, 2018.

(51) Int. Cl.
*A61B 3/032* (2006.01)
*G16H 10/60* (2018.01)
*G16H 30/20* (2018.01)
*G16H 50/20* (2018.01)
*A61B 3/024* (2006.01)
*A61F 9/08* (2006.01)

(52) U.S. Cl.
CPC ............ *G16H 10/60* (2018.01); *G16H 30/20* (2018.01); *G16H 50/20* (2018.01); *A61F 9/08* (2013.01)

(58) Field of Classification Search
CPC ......... G06F 3/04883; G06F 2203/0381; G06F 3/04886; G06F 1/1656; G06F 3/0485; G06F 1/1616; G06F 1/1632; G06F 1/1662; G06F 3/015; G06F 3/023; G06F 3/0231; G06F 3/04845; G06F 3/04847; G06F 3/0488; G06F 3/0489; G06F 3/04817; G06F 1/1686; G06F 3/0482; G06F 3/1454; G06F 3/04812; G06F 3/041; G06F 3/033; G06F 3/16; G06F 1/1643; G06F 2203/04104; G06F 3/04892; G06F 3/165; G06F 16/285; G06F 2203/04806; G06F 3/005; G06F 3/0484; G06F 1/1626; G06F 16/9535; G06F 2203/012; G06F 2203/04802; G06F 2203/04808; G06F 3/0487; G06F 3/167; G06F 12/0207; G06F 12/084; G06F 12/0842; G06F 12/0875; G06F 16/5854; G06F 21/32; G06F 2203/011; G06F 2203/04804; G06F 2212/1024; G06F 2212/302; G06F 2212/401; G06F 2212/455; G06F 3/0338; G06F 3/0655; G06F 3/1446; G06F 40/12; G06F 1/203; G06F 1/206; G06F 16/9537; G06F 2203/0384; G06F 3/02; G06F 3/03547; G06F 1/00; G06F 1/1613; G06F 21/31; G06F 21/604; G06F 21/6218; G06F 2111/02; G06F 2203/013; G06F 2203/04108; G06F 2203/04805; G06F 2221/2111; G06F 3/0362; G06F 3/038; G06F 3/0416; G06F 3/0421; G06F 3/0425; G06F 30/20; G06F 9/451; G06F 1/16; G06F 1/1673; G06F 1/1694; G06F 1/3203; G06F 1/3218; G06F 2203/0331; G06F 3/01; G06F 3/021; G06F 3/0227; G06F 3/0321; G06F 3/0354; G06F 3/03545; G06F 3/0383; G06F 3/1407; G02B 27/0172; G02B 27/017; G02B 27/0093; G02B 2027/0178; G02B 2027/0187; G02B 2027/0138; G02B 2027/014; G02B 2027/011; G02B 17/086; G02B 2027/0118; G02B 2027/0174; G02B 27/0176; G02B 5/04; G02B 17/0896; G02B 27/0101; G02B 27/01; G02B 2027/0141; G02B 2027/0134; G02B 2027/0123; G02B 27/0179; G02B 26/026; G02B 27/0103; G02B 26/10; G02B 5/32; G02B 2027/015; G02B 5/3025; G02B 27/283; G02B 27/141; G02B 2027/0125; G02B 27/02; G02B 27/286; G02B 17/0856; G02B 2027/0107; G02B 2027/0109; G02B 27/0955; G02B 5/208; G02B 13/0055; G02B 27/0081; G02B 27/30; G02B 5/20; G02B 5/30; G02B 2027/0132; G02B 25/001; G02B 26/0833; G02B 26/101; G02B 3/08; G02B 2027/0112; G02B 2027/0114; G02B 2027/0183; G02B 6/0016; G02B 6/0035; G02B 2027/013; G02B 2027/0147; G02B 2027/0185; G02B 5/1866; G02B 5/1876; G02B 5/3083; G02B 2027/0154; G02B 2027/0181; G02B 27/106; G02B 27/143; G02B 3/0006; G02B 17/08; G02B 2027/0127; G02B 2027/0198; G02B 27/0961; G02B 27/104; G02B 27/108; G02B 27/1086; G02B 27/12; G02B 6/00; G02B 6/0026; G02B 6/105; G02B 17/006; G02B 2027/012; G02B 2027/0129; G02B 2027/0156; G02B 27/0018; G02B 3/04; G02B 13/004; G02B 13/0065; G02B 13/04; G02B 13/10; G02B 13/16; G02B 13/22; G02B 2027/0105; G02B 2027/0163; G02B 23/125; G02B 27/0025; G02B 27/026; G02B 27/0922; G02B 27/14; G02B 27/142; G02B 27/146; G02B 3/0056; G02B 30/00; G02B 30/22; G02B 5/09; G02B 5/1823; G02B 5/1857; G02B 5/1871; G02B 6/0023; G02B 6/0036; G02B 6/0038; G02B 6/005; G02B 6/0076; G02B 6/29325; G02B 6/34; G02B 7/008; G02B 9/34; G02B 17/023; G02B 2027/0196; G02B 21/0012; G02B 21/365; G02B 26/0816; G02B 27/0911; G02B 27/0966; G02B 27/0972; G02B 27/123; G02B 30/26; G02B 13/0015; G02B 13/0085; G02B 13/06; G02B 17/004; G02B 17/0605; G02B 2027/0145; G02B 26/004; G02B 26/06; G02B 26/105; G02B 27/0075; G02B 27/0149; G02B 27/0977; G02B 27/10; G02B 27/145; G02B 27/18; G02B 27/28;

G02B 27/646; G02B 30/20; G02B 30/27;
G02B 30/31; G02B 30/34; G02B 5/1885;
G02B 5/23; G02B 5/3016; G02B 7/005

See application file for complete search history.

(56) References Cited

U.S. PATENT DOCUMENTS

| 2012/0162549 A1* | 6/2012 | Gao | G02B 6/003 |
| | | | 359/651 |
| 2012/0206335 A1* | 8/2012 | Osterhout | G06F 1/163 |
| | | | 345/156 |
| 2013/0162632 A1* | 6/2013 | Varga | H04N 13/383 |
| | | | 345/419 |
| 2015/0193984 A1 | 7/2015 | Bar-Zeev et al. | |
| 2018/0325618 A1 | 11/2018 | Justin et al. | |

\* cited by examiner

AUGMENTED AND EXTENDED REALITY GLASSES FOR USE IN SURGERY VISUALIZATION AND TELESURGERY

COPYRIGHT NOTICE

A portion of this disclosure contains material that is subject to copyright or trademark protection. The copyright and trademark owner has no objection to the facsimile reproduction by anyone of this patent document as it appears in the U.S. Patent and Trademark Office, patent file or records, but reserves all copyrights whatsoever in the subject matter presented herein. The trademark names of the systems herein are those selected by the inventors but are not exclusive of names which could be used.

CROSS REFERENCE

This application is based on and claims priority to U.S. Provisional Patent Application No. 62/907,300 filed Sep. 27, 2019. It is also a continuation-in-part of U.S. patent application Ser. No. 15/073,144 filed Mar. 17, 2016, which issued on May 1, 2018 as U.S. Pat. No. 9,955,862, U.S. patent application Ser. No. 15/940,561 filed Mar. 29, 2018, which issued on Oct. 30, 2018 as U.S. Pat. No. 10,111,583, and U.S. patent application Ser. No. 16/173,719 filed Oct. 29, 2018, all of which claim the benefit of U.S. Provisional Patent Application No. 62/134,422 filed Mar. 17, 2015; of U.S. patent application Ser. No. 15/962,661 filed Apr. 25, 2018, which claims the benefit of U.S. Provisional Patent Application No. 62/489,801 filed Apr. 25, 2017; of U.S. patent application Ser. No. 16/511,202 filed Jul. 15, 2019, which claims the benefit of U.S. Provisional Patent Application No. 62,697,854 filed Jul. 13, 2018; and of U.S. patent application Ser. No. 16/511,451 filed Jul. 15, 2019. All are incorporated herein by reference.

BACKGROUND OF THE INVENTION

Field of the Invention

This invention relates generally to augmented and extended reality glasses, and more particularly, but not by way of limitation, to augmented and extended reality glasses for use in surgery visualization.

Description of the Related Art

There is a need for surgeons to be able to access real-time and pre-recorded computer-generated and/or camera images in the operating room. To address this need, virtual reality (VR) surgical or diagnostic headsets have been attempted to be used. However, VR totally immerses the user into the images presented, essentially totally blocking and replacing the user's field of vision of the real-world, often called the real-reality (RR) with virtual images. Such systems are defined by their replacement of the reality around the user with a total virtual substitute. This immersion locks the surgeon into a virtual space that is not easy to extract from in case of emergency.

For example, some virtual reality surgery systems include immersive goggles with micro-displays facing the user's eyes, much like small televisions, and noise-cancelling headphones. The micro-displays completely replace the surgeon's view of the operating room and outside world. The surgeon is thus cut-off from the surgery room and the video from the micro-displays is surrounded by complete darkness. Such virtual reality surgery systems are designed as a 3D mobile theater, essentially simulating holding two small televisions in front of the user's eyes while completely eliminating outside light and sound.

Such existing virtual reality surgery systems are generally uncomfortable and must be worn tight on the head, blocking out reality. VR systems seal out real-word light, sound, and air around the surgeon's eyes and cheeks, making the device hot and uncomfortable. The heat generated by the surgeon wearing the VR headset and from the headset itself often causes condensation on the interior lenses, which makes the images appear foggy and requires the surgeon to take of the VR headset for cleaning during the surgery. Clearing the lenses typically only helps temporarily. Some such systems use a trackpad that is turned 90 degrees from the user interface, so that swiping forward actually moves right and swiping backward moves left. This can be frustrating for the user, particularly if the user is left-handed. Moreover, typing within a VR headset menu is a painstaking and time-consuming chore, making entering HIPPA compliant passwords for sensitive data difficult. Furthermore, such virtual reality systems are typically heavy, with most of the weight forward on the head, making it uncomfortable for the user.

To address these concerns, augmented/extended reality (AXR) surgical systems have been introduced. Whereas virtual reality immerses the user into the images presented and closes RR, AXR permits the user to see RR and what is actually happening in the user's world and then adds computer-generated, computer-manipulated, or secondary camera images to RR. Thus, while virtual reality completely covers and replaces the user's field-of-vision with virtual images, augmented/extended reality provides the user with vision of the real-world plus an overlay of computer-generated and/or manipulated photographic imagery or video ("virtual") images, which positions the user in the RR with virtual images added.

In an operating environment, an augmented/extended reality system permits the surgeon to both view and have magnified the virtual image or area of operation, while still having a sense of the operating or diagnostic room and being with all the other things happening in that space. The problem with current AXR surgical systems is that they offer a small field of vision on a heavy wearable that is often tethered to the system by a large cord, limiting the surgeon's movements and putting strain on the surgeon's neck and back. Furthermore, current AXR surgical systems must block out a great deal of ambient light to make the AXR images visible and are difficult to see in daylight or highly-lighted conditions, making the systems function more like a virtual reality system than an AXR system.

Based on the foregoing, it is desirable to provide a true AXR surgery system that provides an overlay of computer-generated images while maintaining a sufficient real-world view.

It is further desirable for the system to be lightweight, comfortable, untethered, and is feature- and user-friendly It is further desirable for the system to offer a wide field of vision.

While the focus of this invention is on its application to the medical and surgery fields, it is further desirable for the same techniques to be utilized in other sectors where wearing a lightweight, comfortable, untethered, feature- and user-friendly AXR headset would be of benefit.

SUMMARY OF THE INVENTION

In general, in a first aspect, the invention relates to an AXR surgical system comprising: a wearable device comprising one or more micro-displays, one or more lenses, where the micro-displays are capable of projecting images onto the lenses, a head-tracking subsystem, and an eye-tracking subsystem; and a central processing unit in communication with and capable of controlling the micro-displays, lenses, head-tracking subsystem, and eye-tracking subsystem. The system may be capable of displaying images on the lenses with a position based on a user's head position as tracked by the head-tracking subsystem and the user's eye position as tracked by the eye-tracking subsystem, while allowing the user to see through the lenses where the images are not being projected.

The lenses may comprise a reflective layer and a layer of cholesteric liquid crystal comprising a plurality of pixels where each pixel is capable of independently becoming opaque. The system may be capable of selectively making pixels opaque only where images are projected by the micro-displays, while any pixels located where the images are not projected remain see-through. The AXR surgical system may further comprise at least one collimator located between the micro-displays and the reflective layer such that the at least one collimator is capable of concentrating rays from the micro-displays in an eye box while utilizing less resolution in a periphery.

The camera lenses may be capable of capturing a wider field of vision than the micro-displays may be capable of projecting. In this instance, the reduced field of vision may be comprised of the view where user is gazing as tracked and analyzed by the eye tracking system. The wearable device may further comprise one or more forward-facing cameras, where the images projected by the micro-displays are at least partially images obtained from the forward-facing cameras. The wearable device may further comprise one or more at least partially downward-facing or upwards-facing cameras, where the images projected by the micro-displays are at least partially images obtained from the at least partially downward-facing or upwards-facing cameras, which angle may be adjustable.

The AXR surgical system may further comprise one or more microphones in communication with the central processing unit, where the system is capable of being controlled via voice input via the microphone, input from the eye-tracking subsystem, or a combination of voice input via the microphone and input from the eye-tracking subsystem. The microphones may have noise cancelling features capable of reducing ambient noise. The wearable device may further comprise one or more batteries. The wearable device may further comprise a remote communication device such that the wearable device is wireless.

The system may be in communication with one or more second systems such that one or more remote users can view the images from the system on the one or more second systems and communicate will the user and other remote users. The images projected by the micro-displays may be from preoperative imaging, and the system may be capable of aligning the images with a patient.

The system may further comprise a remote camera system in wireless communication with the wearable device, where the images come from the remote camera system. The remote camera system may be mounted on a six-axis cobotic arm, which may be in communication with the system such that the cobotic arm is controlled by the user.

Figure 1:
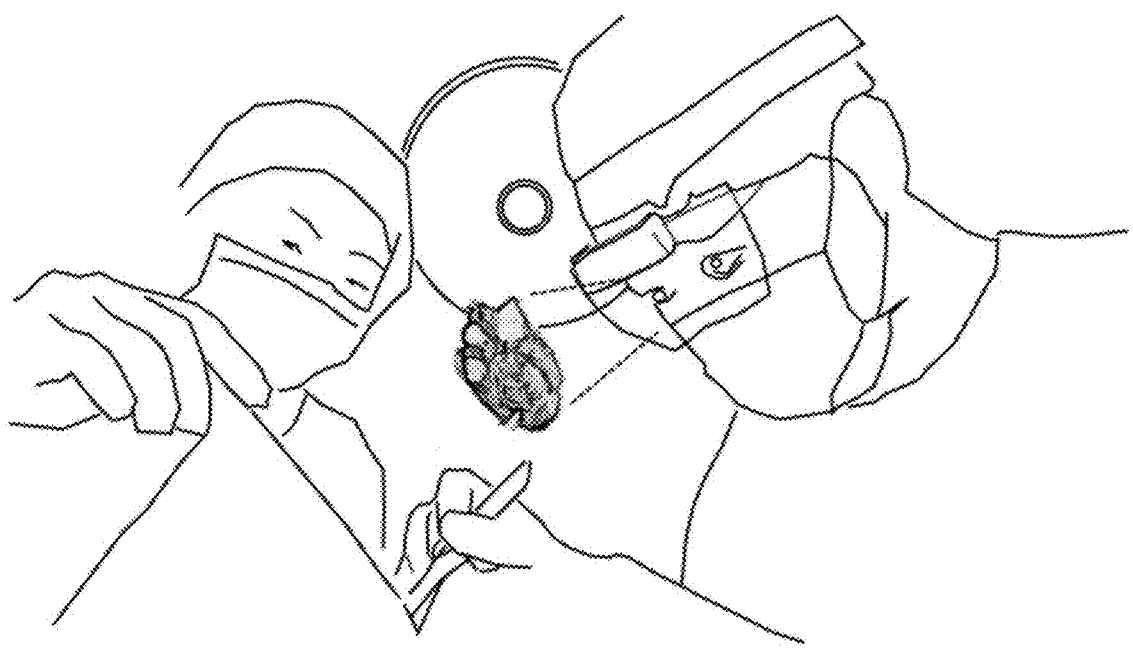
FIG. 1 is a perspective view of the AXR surgical system in use.

Other advantages and features will be apparent from the following description and from the claims.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

"Augmented and Extended Reality" (AXR) is defined herein in its common scientific use, which may include an interactive experience typically in a see-through headset with lenses of a real-world environment where the objects that reside in the real world are enhanced by computer-generated perceptual images and information, sometimes across multiple sensory modalities, including visual, auditory, haptic technologies, somatosensory, and/or olfactory.

"Extended Reality" is defined in its common scientific use, which is typically an umbrella term encapsulating augmented reality (AR) and/or virtual reality (VR) and/or mixed reality (MR) and/or real reality (RR) and everything in between. It may also include combined environments and human-machine interactions generated by computer technology such as 6DoF and SLAM, and artificial intelligence (AI), including machine learning (ML), where the 'X' represents a variable for any current or future spatial computing technologies, including digital content of any sort; for instance, in the medical field, a 3D MRI or CT scan images or data visualizations, like patient vitals, superimposed on an AR headset.

"Six Degrees of Freedom" (6DoF) is defined herein in its common meaning, including the way virtual objects can be moved in virtual space in AR. There are six total degrees of freedom in placing virtual images in AR. Three (3) correspond to rotational movement around the x, y, and z axes, commonly termed pitch, yaw, and roll. The other three (3) correspond to translational movement along those axes, which can be thought of as moving forward or backward, moving left or right, and moving up or down.

"Inertial Measurement Units" is used herein in its common scientific meaning, including referencing devices for measuring rotational movements, such as an accelerometer, a gyroscope, and a magnetometer, all located within the headset. These IMUs may measure the headset's velocity, orientation, and gravitational forces to infer rotational orientation and movement.

"Haptic technologies" is used herein in its common scientific meaning and is sometimes called kinaesthetic communication or 3D touch. It may also refer to any technology which may create an experience of touch by applying forces, vibrations, or motions to the user or to an object. Haptics may enable users to feel the sense of touch via vibrations of forced motion. Haptic technologies can be used to create virtual objects in a computer simulation or virtual space, or to control those virtual objects, and may be used to enhance remote control of machines and devices (telerobotics). Haptic devices may incorporate tactile sensors that measure forces exerted by the user on the interface. This technology may employ touch sensors for control.

"Artificial Intelligence" (AI), sometimes called "Machine Learning" (ML), is used herein in its common scientific meaning, including referring to the simulation of human intelligence in machines that are programmed to think like humans and mimic their actions and decisions. The term may also be applied to an augmented reality headset that exhibits traits associated with a human mind, such as learning and/or problem-solving. AI may enable AR to interact with the physical environment in a multidimensional way. For instance, AI may permit object recognition and tracking, gestural input, eye tracking, and voice command recognition to combine to let the user manipulate 2D and 3D objects in virtual space with the user's hands, eyes, and/or words.

"Object Recognition" (OR) or "Object Identification" (OI) is used herein in its common scientific meaning, including a computer vision technique for identifying objects in images or videos. Object recognition may be a key output of deep learning and AI algorithms. When humans look at a photograph or watch a video, we can readily spot people, objects, scenes, and visual details. OR/OI does this from visual analysis based on a neural network algorithms reconciliation with pre-existing information.

"Simultaneous Localization and Mapping" (SLAM) is used herein in its common scientific meaning, including a technology that understands the physical world through a 3D grid of feature points. SLAM maps what the camera and sensors see in three dimensions with correct spatial information and distancing. This may make it possible for AXR applications to recognize RR 3D objects and scenes, as well as to instantly track motion in the RR, and to overlay digital interactive augmentations.

The term "image(s)" or "virtual image(s) or "imaging" or "virtual objects" or "AXR imaging" is defined for the purpose of this patent as visualization of either 2D images or video or 3D images or video. The definition also includes the concept that one or more 2D images can be viewed in stereoscopy to create one or more virtual 3D perspectives. Further included in the "image(s)" definition, herein, is the idea that AXR 3D models may be viewed as a single or series of 2D images, as in a still picture or video, or a single or series of stereoscopic 3D images, as in a 3D images or video. The 3D effect may be created in the AXR headset by using an off-set paired perspective of a 3D model. In addition, 3D models in AXR can be viewed from different perspectives by the user or multiple users can view the same image from multiple perspectives.

The term "wireless" as used herein means the electromagnetic transfer of information between two or more points which are not connected by an electrical conductor, or a communication by technologies, such as light, magnetic, or electric fields, or the use of sound. The term "wired" communication as used herein includes all methods of wireline communication including, but not limited to, directly connected devices, telephone networks, ethernet connections, cable networks, internet access, fiber-optic communications, and waveguide (electromagnetism) connections.

In general, in a first aspect, the invention relates to an augmented and extended reality (AXR) surgical system. The system may comprise a wearable device 1, such as a head mounted display (HMD) or glasses, that provides the user with virtual reality (VR), augmented reality (AR), and/or mixed-extended reality (XR) for surgery visualization, as shown in FIG. 1. This may allow the user to access 2D or 3D imaging, magnification, virtual visualization, six-degrees of freedom (6DoF) image and simultaneous localization and mapping (SLAM) management, and/or other images while still viewing real reality (RR) and thus maintaining a presence in the operating room.

Figure 2:
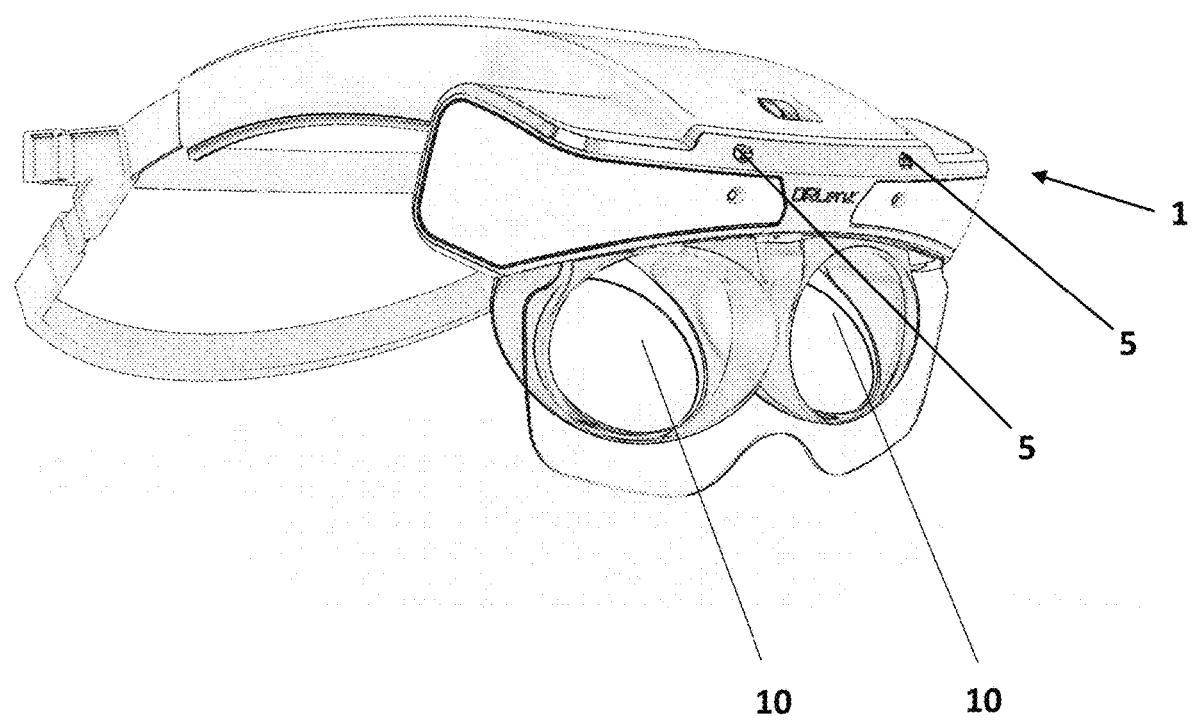
FIG. 2 is a perspective view of the AXR surgical system headset.
Figure 3:
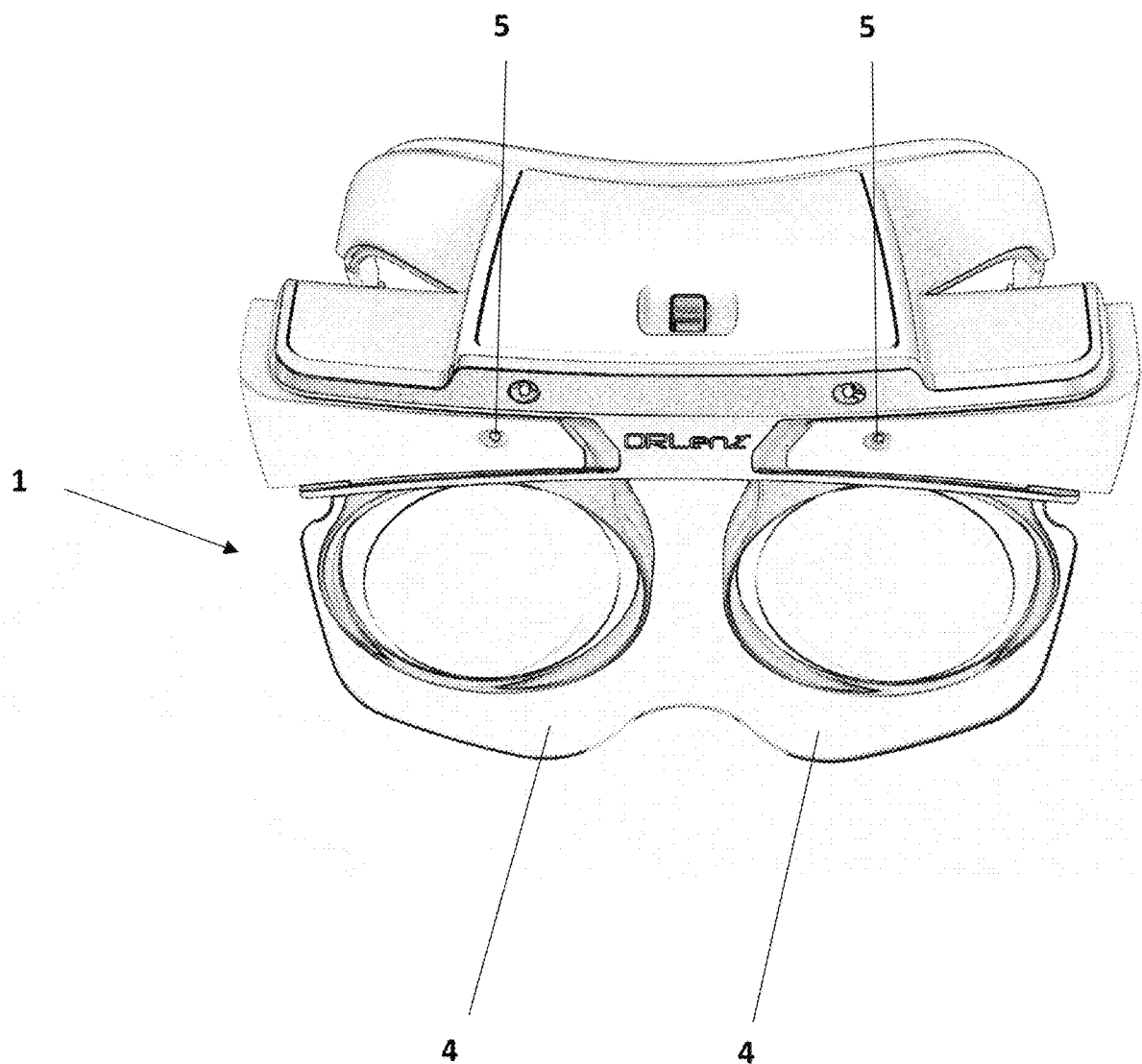
FIG. 3 is a front view of the AXR surgical system headset.

The system may comprise one or more micro-displays 2, a head-tracking subsystem 3, an eye-tracking subsystem 4, and one or more cameras 5, all of which may be included on the wearable device 1. The system may further comprise one or more lenses 10, where the micro-displays 2 are capable of projecting images on the lenses 10, where the images may be reflected back to the user's eyes. For example, as shown in FIGS. 2 and 3, the wearable device 1 may be a head mounted display with a pair of lenses 10, one in front of each of the user's eyes. One or more micro-displays 2 may be located above the user's eyes and may be pointed toward the lenses 10. The cameras 5 may provide image input, while the head-tracking subsystem 3 and the eye-tracking subsystem 4 may provide positional input, allowing the system to project the desired images to the desired location for the user to view the images. Additional image input may be provided from other sources. All components may be controlled by a CPU, which may be located on the wearable device 1 or remotely. Other components may include additional central processing units, one or more graphics processing units, one or more digital signal processors, firmware, hardware, software, and/or memory components, as well as other desired components. The high-level components may control the features and functions of the AXR headset 1, including, but not limited to its cameras 5, micro-displays 2, lenses 10, sensors, communications, and subsystems.

The system may be capable of displaying both real reality and computer-generated images (CG or CGI) or computer captured and manipulated images (CMI), effectively creating the illusion of AXR. In this context, CMI may mean previously recorded, captured, or created images or video from a different reality than the RR displayed in the AXR headset. Additionally or alternately, the system may be capable of functioning as a "heads-up" system, allowing the user to look at the images on the micro-displays 2 or look beyond the display to the larger environment of the real-world operating room and attendants. Thus, the system may provide a full field of vision, unlike existing systems. Specifically, for example, the micro-displays 2 may provide a wide field of vision of, for instance, 120 degrees, namely 60 degrees horizontal and 36 or more 65 degrees vertically in each eye, or other desired field of vision. This may allow a high angular resolution of 60 pixels per degree in the eye box, which is the highest resolution the eye can distinguish at 20/20. Humans have a slightly over 210-degree forward-facing arc of their visual field. The cameras 5 of the system may capture all or most of the human forward-facing degrees, when needed. Correspondingly, the user may view 120 degrees field-of-view (FOV) of AXR through the cameras 5 and micro-displays 2 and 210 degrees of RR with the system functioning as a heads-up display (HUD). This field of vision may actually be even larger from a practical standpoint as the user may, for example, look down at his or her hands, which are outside the AR/RR presented field of vision. The availability of viewing the real reality environment may be important to a surgeon when he or she is trying to pick up a tool or adjust his or her hands during surgery. This type of viewing is not possible with existing VR systems, which require the eye of the surgeon to be always exactly aligned, something that might well prove exhausting in a lengthy surgery.

The cameras 5 may be two on-board 4K or higher resolution cameras and may, as noted above, capture a wide field-of-view, such as 180 to 210 degrees forward-facing vision. This oversampling of the field of vision may then be stored per frame and used in conjunction with the eye-tracking subsystem 4 to present the actual field of vision depending on the user's gaze. In this fashion, the system may use images from the entirety of the 180 degrees captured or a reduced sample of the entire captured cameras degrees FOV. As the system's eye tracking follows the eye of the surgeon as his or her eyes move, the system may be able to provide imagery from the fully captured 180 or more degrees.

Alternatively, the virtual images projected by the micro-displays 2 may come from existing data, pictures, graphs, videos, MRI's, CT scans, or other pre-recorded images or information.

Figure 5:
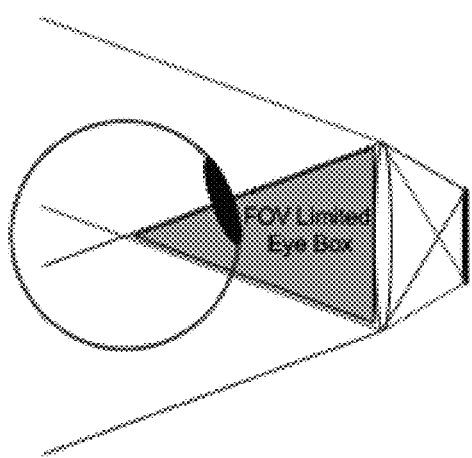
FIG. 5 is a diagrammatic illustration of an eye box.

The large field of vision of the system may result in a large eye box for the user, as shown in FIG. 5. The eye box of any AXR or VR system may be crucial as it may serve as the connection between the device and the user. The eye box of the system may be large enough to provide comfortable viewing of the full field of vision with the highest resolution even if the headset moves while wearing. Further, the eye box of the system may be large enough to account for eye relief for the user, including allowances for brow size and how deep-set the user's eyes are, as well as clearance for eyeglasses and allowances for lateral pupil movement. As used herein, the term "eye box" is analogous to the term "eye relief" of a typical optical instrument, such as a telescope, a microscope, or binoculars, which is the distance from the last surface of an eyepiece within which the user's eye can obtain a full viewing angle. If a viewer's eye is outside this distance, a reduced field of view may be obtained. Thus, the smaller eye box of previous VR systems is inferior to the large eye box of the current system.

Figure 6:
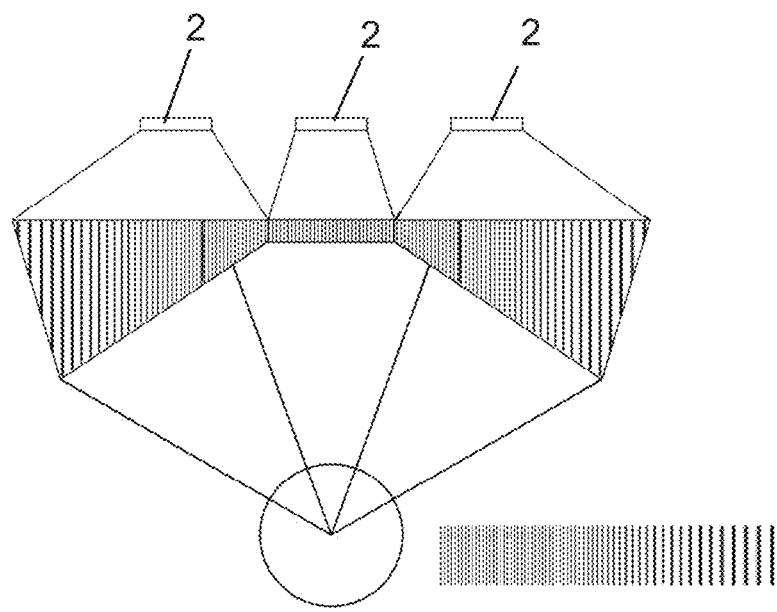
FIG. 6 is a diagrammatic view of the micro-displays.

The eye box of the current system may be as much as 20×20 mm×60 p/p/d. This may be achieved by providing three micro-displays 2 having the outer two displays 2 sharing pixels with the central display 2 through the system's algorithms, as shown in FIG. 6. To the foveal vision of the eye, where the highest resolution imagery is perceived on the retina, the system may present approximately 50 degrees horizontal by 20 degrees vertical field of vision at 60 pixels per degree. The remainder of the field of vision may have approximately 20 pixels per degree, which may be equal to or better than the acuity in the outer parts of the retina. The lenses 10 may be concave in construction, aiding to focus and enlarge the surgeon's eye pupil view for the biggest possible eye box. Thus, it is almost impossible for the user to lose the view of the AXR or surgery visualization image due to the large FOV and very high resolution of the system.

The resolution of the micro-displays 2 may specifically be 22 pixels per degree, or 2560×1440 (Quad HD); 25 pixels per degree, at 3200×1440; 60 pixels per degree at 7200× 1600; or any other desired resolution. The luminance may be 1,000 cd/m2, or higher, while contrast may be 100,000:1 or higher. The micro-displays 2 may support 110 percent of the sRGB color gamut ratio.

The system may utilize voice control, eye tracking, or gesture recognition technologies. Alternatively, one or more of these technologies may be used together in order to access and manipulate a control. This method may allow the user to control the AXR system or other external equipment or systems via wired or wireless connection without requiring input through foot pedals, buttons, hand dials, or other hardwired methods of control. Combining two or more methods of control, i.e. voice with eye tracking, may provide redundancy and ensure proper operation of controls.

The system may utilize a high-resolution high-speed wireless video connection with approximately the same latency as an actual wired system and may be synced with one or more wireless headsets and one or more wired display systems to present a simultaneous view on all the wireless headset(s) and wired display systems from the original camera(s) source. The one or more original source cameras may be mounted on the AXR headset 1 or as a part of an external cameral systems like the 3D 4K camera system described herein. Thus, the networked headsets and monitors of the system may allow multiple participants to see and experience the same surgery or diagnostic view or provide an experienced surgeon with the ability to remotely assist an immediately present or remote inexperienced surgeon. This technique may be used to also teach and train healthcare workers. By continually monitoring and transmitting the image of a surgery between two or more distant users, the system may enable remote virtual telemedicine collaboration between multiple surgeons, assistants, techs, students, or others.

The system may optionally exactly align the CG or GMI image with the real environment. This alignment may be accomplished by creating an overlay, which permits the alignment of preoperative CT or MRI 3D images with the currently treated patient's body, body parts, or internal organs. In this fashion, while wearing the AXR headset 1, the surgeon may be able to both view the whole person in RR while seeing images of internal items like the person's internal organs, blood, bone, or tissue while using 6DoF, SLAM, and gesturing recognition technologies or others techniques mentioned herein where the user can change the orientation and registry of the virtual image to match the real organ. The system may utilize dynamic opacity, described below, making the AXR image either a complete view, blocking RR and the real organ, or a partial transparency, where the AXR organ image or model and the RR organ can be viewed at the same time to align them together. In this fashion, surgery precision may be increased as the areas identified in the lab on the CT or MRI can be superimposed over the real organ to know exactly where to inject, incise, resect, or otherwise operate.

Figure 7:
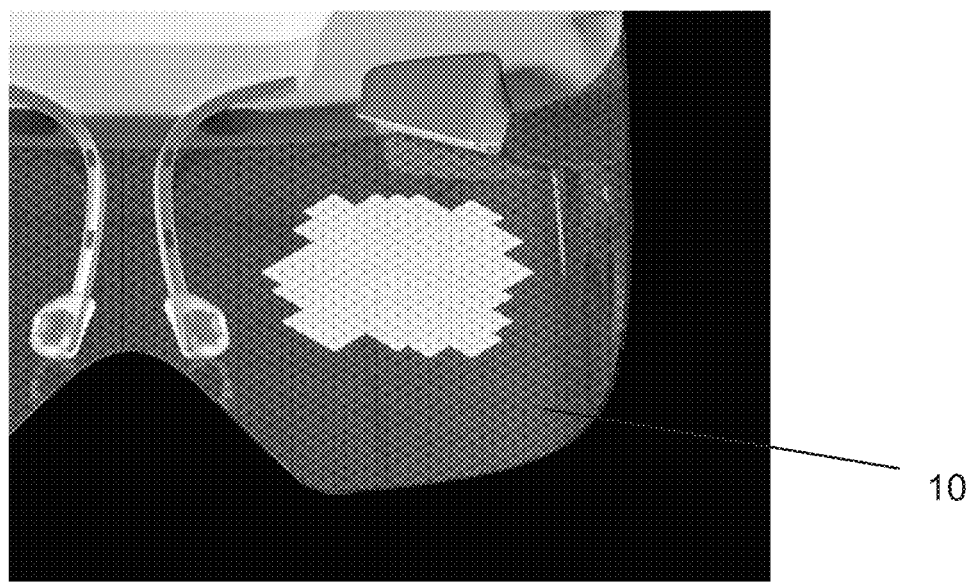
FIG. 7 is a close-up view of the dynamic opacity.

The dynamic opacity subsystem that allows the system to function as a true AXR system may be provided by a multilayered lens 10, which may be part of the wearable device 1. Typically, when using a reflected image on a see-through lens in sunlight or bright light conditions, the reflected image can be washed out. Other systems solve this problem with dark lenses. Having the lens shaded all the time, however, makes the wearer vulnerable to falling or tripping over unseen obstacles. The dynamic opacity of the lens 10 of the current system, however, may only obscure that portion of the lens 10 where the eyes are viewing the AXR image as alpha matte composites, meaning the combining of several images from different sources into a single image. FIG. 7 illustrates the dynamic opacity of the present system.

The system may utilize alpha matte software that works in conjunction with eye-tracking technology and software to map the user's eye gaze and adjust not only the image, but also move or vary the opacity of the exterior of the lens 10 where the eyes are gazing and the image is projected. In addition, the software may automatically or manually adjust the opaqueness of the alpha matte display up or down to meet ambient lighting conditions.

Figure 4:
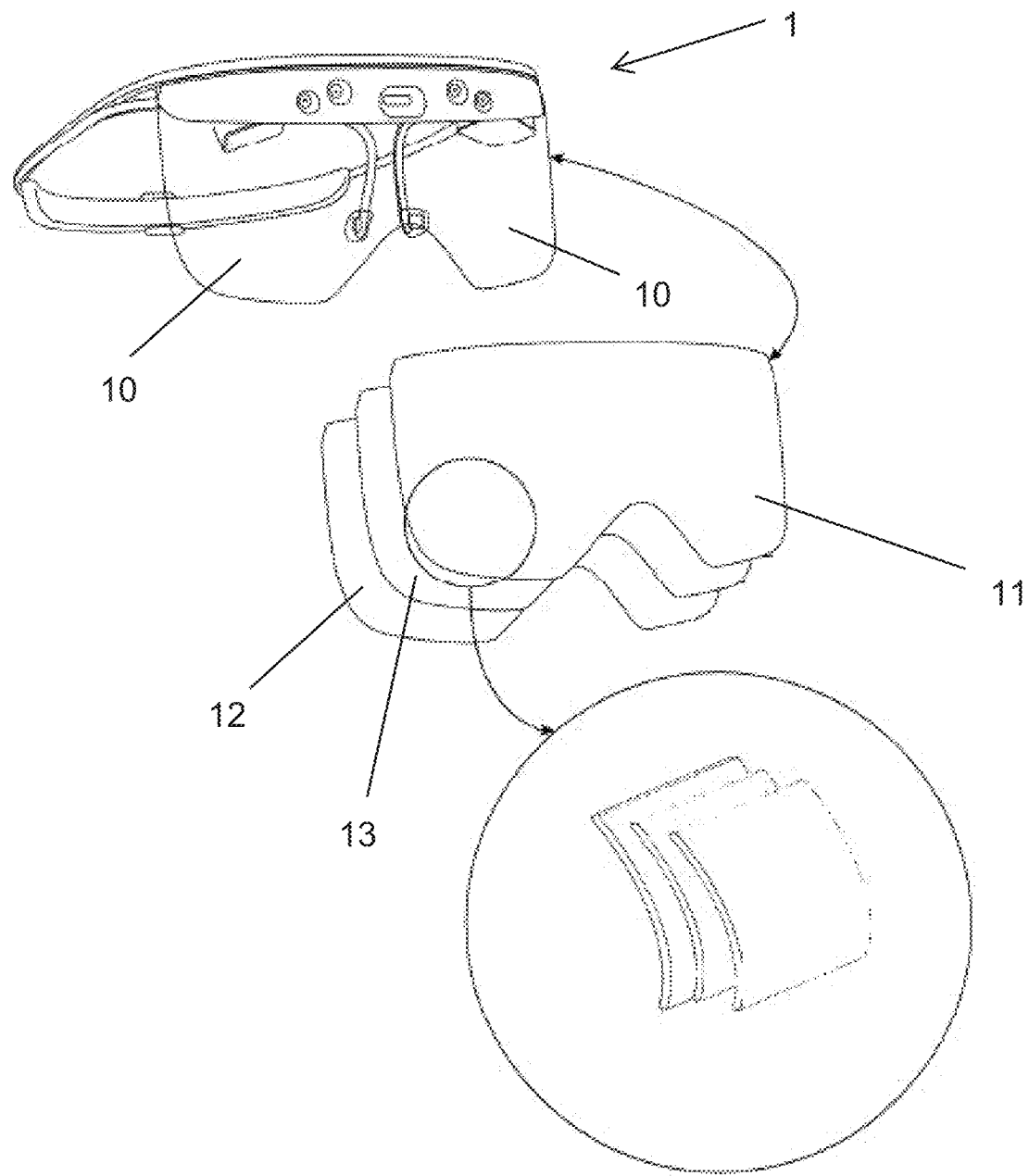
FIG. 4 is an exploded view of the lenses.

The lens 10 may have multiple layers, as shown in FIG. 4, with dynamic opacity provided on the outer layer 11, furthest from the user's eye. This layer 11 may be pixelated, which may permit the system to create a shadow or mirrored image of whatever virtual image is being displayed. This may provide a backdrop for the virtual image, blocking out light that might otherwise wash out the image. The remainder of the layer 11, where the image is not being displayed, may remain clear. Alternately, all of the pixels of the layer 11 may be activated, making the layer 11 fully obscure and blocking out the RR. This may allow the user to use the system as a VR-type headset, but with the ability to see his or her hands to pick up tools and instruments in the periphery of the glasses where the lens does not obscure the RR vision. Thus, surgeons who do not like surgery room distractions can chose to engage the dynamic opacity via voice command and make the system more like a VR headset, blocking out the view through the lens 10 behind the AXR image or video when ultra-concentration is needed. At other times, the surgeon can choose to make the dynamic opacity off or clear in the portion of the lens where there is no reflected image, to use the system in normal mode, where only the AXR image is shadowed form the back. The dynamic opacity of the lens 10 may provide a buffer between the displayed image and exterior light, giving the AXR image greater brightness to the eye. The system may allow the dynamic opacity to be enabled automatically, under pre-set conditions, manually, or with voice, gesture, or eye tracking command.

The layer 11 may comprise a plurality of pixels of cholesteric liquid crystal, each of which may be independently capable of becoming clear or opaque, or in between, as desired.

The lens 10 may further comprise a reflective layer 12, which may be a lens or a coating. The reflective layer 12 may be located closest to the user's eye and may be the surface upon which images projected by the micro-displays 2 for reflection back to the user's eyes. An anti-reflective layer 13 may be positioned next and may be a layer or optical coating that may prevent unwanted artifacts, such as ghosting. The lens 10 may further comprise one or more collimators 14. The collimator 14 may be a separate layer included in the lens 10; additionally or alternately, layer 11 or layer 12 may have aspects of a collimator, and thus may function as the collimator 14; additionally or alternately, the collimator 14 may be a separate lens located between the micro-displays 2 and the reflective layer 12. The collimator 14 may be capable of concentrating rays from the micro-displays 2 in the eye box while utilizing less resolution in the periphery for an overall highest resolution and field of vision.

The eye tracking subsystem 4 may work through hardware and software. The software may be connected to the system's GPU working in connection with the system's modular controller. The eye tracking may be captured by infrared light being projected into the user's eye, which may create a glint or reflection, which may then be captured by one or more IR sensitive cameras 8. The eye tracking subsystem 4 may be capable of capturing the glint from the eye from 30 frames per second to 500 frames per second. This information may be stored in real-time in the CPU and DSP, and then processed into a virtual space represented by x,y,z or Cartesian coordinates. These coordinates may provide the system with the information about where the user's gaze is in relation to the reflective lens and the alpha matte layer so that both stay aligned with the user's gaze. The eye tracking subsystem may be used to map the user's eye gaze and adjust not only the reflected images or video but also the alpha matte image located on the separate plane to keep the alpha combined image aligned with the eye box. Thus, the eye-gaze and the alpha matte layer may be controlled by the eye tracking subsystem 4 to always stay in sync.

Figure 8:
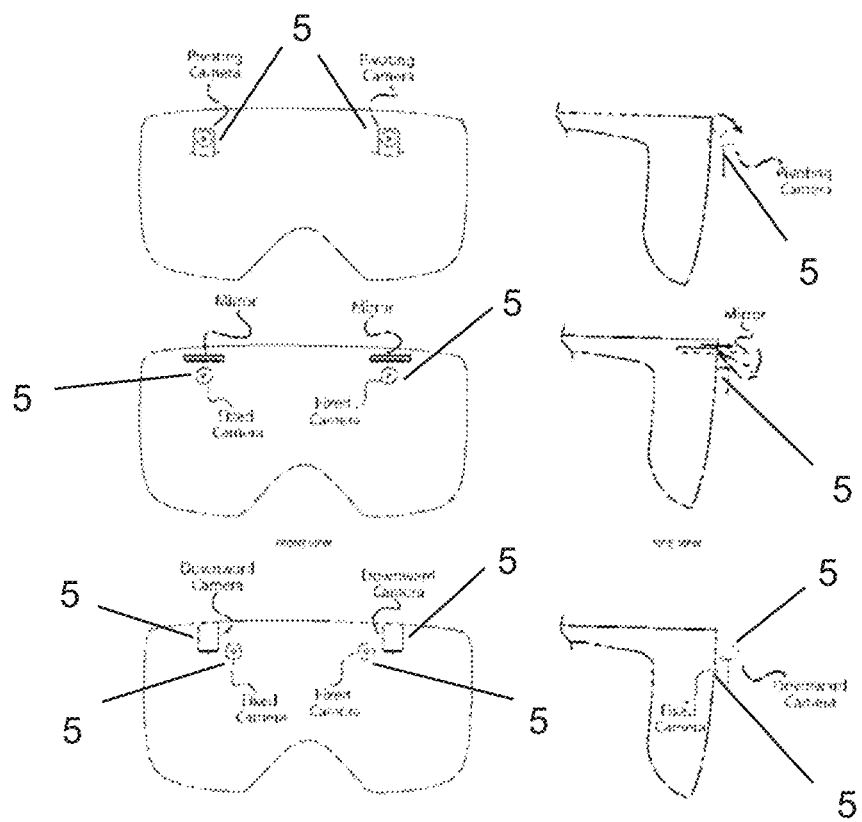
FIG. 8 is a diagrammatic view of three camera options.

As noted above, the cameras 5 may comprise two forward facing cameras 5. Optionally, the system may further comprise two additional cameras 5, which may be adjustable from 60 to 90 degrees. These additional, adjustable cameras 5 may permit the surgeon to operate with his or her head in a comfortable position while the view on the lens 10 is that of straight down. Optional camera configurations are shown in FIG. 8.

Figure 10:
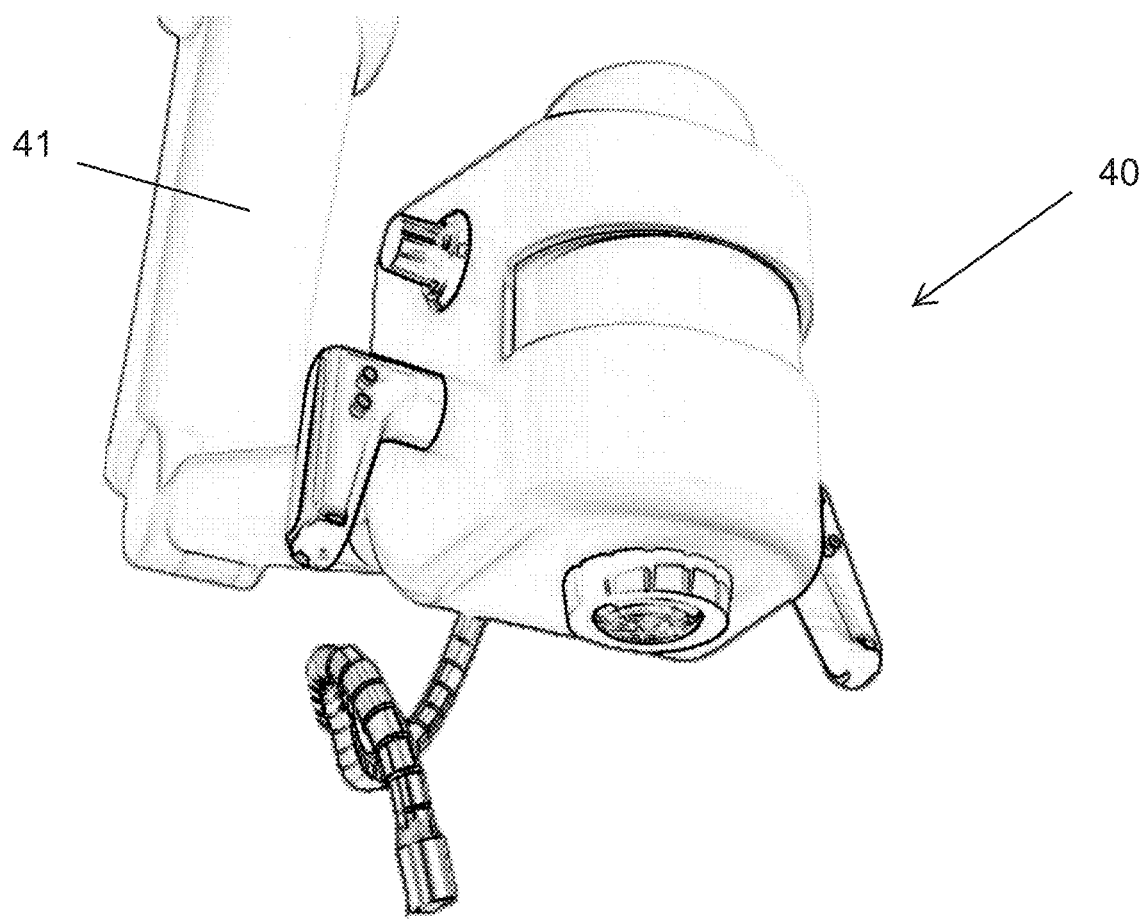
FIG. 10 is a perspective view of a 3D surgical camera with two sensors.
Figure 11:
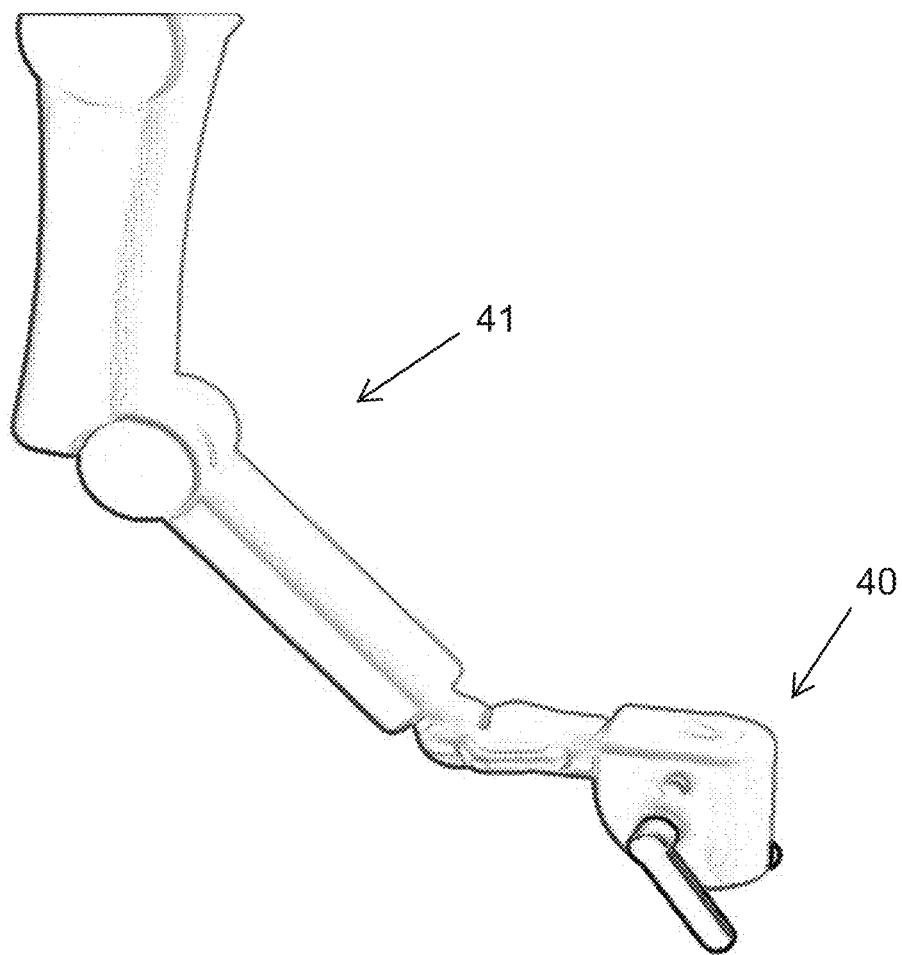
FIG. 11 is a perspective view of the camera on a cobotic arm.

Alternatively, as shown in FIG. 10, the one or more cameras 5 may be housed within their own system 40, like a digital 3D 4K system, and may be connected wired or wirelessly to the AXR headset 1. The camera system 40 may consist of two parallax mounted cameras 5 to create a 3D viewing experience and may be mounted on a six-axis robotic/cobotic arm 41 for surgery use, as shown in FIG. 11. Herein the six-axis arms are called cobotic, which means the combination of robotic automated movement combined with the collaboration of an operator, who may activate and control the cobotic arm 41 by voice control, eye tracking, gesture recognition, haptic technologies, touch, or other control technologies mentioned herein or with a joy-stick. Alternatively, two or more of these controls may work in combination with another for control.

The cobotic arm 41, when voice or otherwise activated using the technologies described herein, may recognize the exact site of the surgery on a patient's body to be viewed during the surgery from pre-programmed information and may travel according to the software and the ability of the six-axis arm 41 to the exact position the camera is needed for surgery. The six-axis arm 41 may be connected to a stationary or movable side-carte component stationed on the floor or connected to a boom on the ceiling or a wall.

The arms 41 may be powered by motors and may be gravity-compensated and may respond to either the touch of an assistant, or by voice command, or any other of the control technologies mentioned herein. The six-axis cobotic arm 41 may receive and transmit sound, light, vision, movement, and/or sensitive sense-of-touch (force tactile transmission) to a remotely located user or controller in real time. The precision motors contained within the cobotic arm 41 may use the haptic sensors or internal algorithms to work with a user's so that, for instance, a slight touch in the direction of its repose may cause the cobotic arm 41 to continue to its position of repose. Likewise, if the arm 41 in a position of repost, a slight push towards another programmed or learned location will cause it to activate the motors to continue to that location. The cobotic arm 41 may also be manually placed in a certain position by a user, and the cobotic arm's controller may remember the exact movement so that it can duplicate that movement automatically upon command by any of the technologies mentioned herein. For instance, if a cobotic arm 41 is manually placed at a surgery location needed for viewing the surgery site, and then, during the surgery the patient developed a bleed or other cause of emergency, the cobotic arm 41 could be activated to move to its repose position. Once the issue was resolved, the cobotic arm 41 with the camera may, on command, return to the exact location needed to continue the surgery. Also, a surgeon or tech may slightly push the robotic arm 41 in one direction, and the cobotic arm 41 would continue to move to that direction until it ended up in the intended position. Likewise, if a surgeon or assistant pulled on an arm 41, it would continue until it reached a predestined spot.

Figure 9:
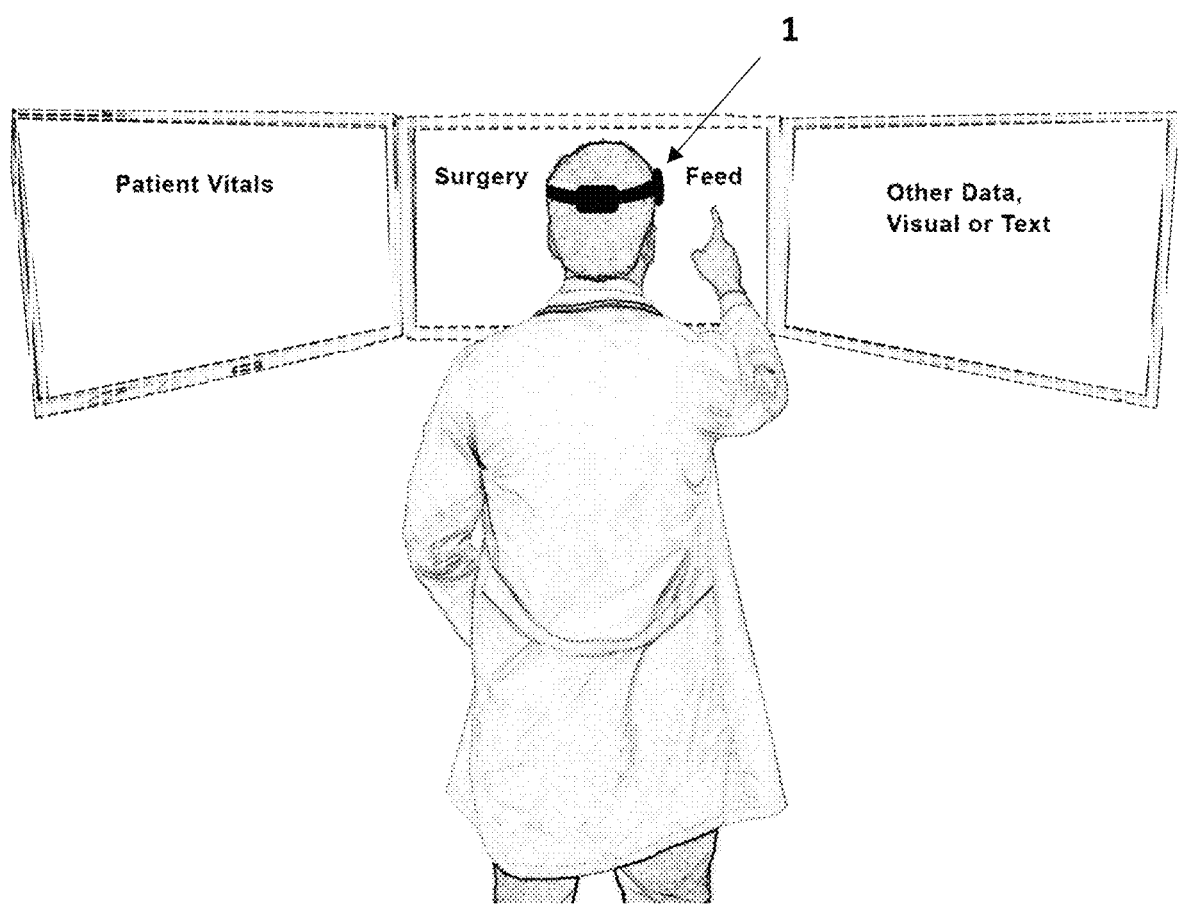
FIG. 9 is a back view of a person wearing the AXR headset, illustrating different views presented by the virtual overlay.

The surgeon may additionally or alternately wirelessly receive a 3D video feed from a digital microscope, providing the surgeon with an alternative surgical video input. The system may be capable of overlaying information, such as text and graphs, in a virtual display over the operating view, as shown in FIG. 9. the system may allow the surgeon or user to control and present the overlayed information, pictures, graphs, or videos in other views inside the headset via a visual presentation subsystem. The visual presentation subsystem, powered by IMU, SLAM, and/or eye tracking technologies, may provide an overlay of vital information, such as text and graphs, in virtual display over the 3D operating view. The visual presentations may be like windows or chyron generated view visible within the AXR FOV and may be virtually presented in a certain pre-set location of the user's view. For example, for an ophthalmologic surgery, the system may display intraocular pressure, cut rate, and flow rate or may show which mode a surgeon is in, such as vitrectomy, extrusion, dense tissue, etc., and may retrieve and track a preloaded surgery plan. For other surgeries, such as vascular, ENT, thoracic/cardiac, or orthopedic, this information displayed may vary depending on the equipment or information useful to the surgeon during the surgery.

Alternatively, the overlay may be used to view preoperative or interoperative images in virtual format, including pictures, videos, MRI's, CT scans, and the like. This information may be visible upon voice command of the surgeon, and the system may provide the user the option of displaying information at the bottom, side, or top of the AXR lens view. In other words, for example, if using eye tracking or head tracking, the surgeon may move his or her head or eyes at a predetermined degree of rotation, for instance 15 or 30 degrees either to the side or up and down. With this turn of the eyes or head, the surgery video feed images may disappear and alternative information like patient vitals may appear. When the surgeon moved his or her head or eyes the opposite way, equipment readouts, preoperative information, or other important information may appear. Likewise, when the surgeon moves his or her head or eyes back, the surgery images may appear to return focus to the surgery. When the surgeon looks a certain pre-set degree downward, the surgery images may disappear, and the surgeon could refocus on the RR patient and surgery. Alternately, the system can be set to leave the information always in view. Thus, a surgeon who does not like distractions can have the option of making a slight head or eye adjustment as needed to see the information. For example, while a retina surgeon is in laser mode, he or she may enable the information display to show power, standby versus on, duration, and intensity.

Optionally, the AXR headset may use IMU, SLAM, eye tracking, and/or other technology to permit the surgeon to move his or her head forward or use an eye movement or other manner of control described herein to cause the z coordinate to reorient to magnify or reduce the surgery image.

For the system to provide these options, the AXR headset 1 may be embedded with SLAM, 6DOF, inertial measurement units (IMU), or eye tracking technology, which may interpret the angle of the user's head or eyes versus the displayed image. Then, when either the eyes or head move to focus on a portion of the image that is originally on the edge of the view, the system may digitally reposition the image to the center of the user's visual field, providing a high-focus view independent of where the image was originally located.

The head tracking subsystem 3 may include an internal array of IMUs 7, which may include one or more accelerometers, gyros, and/or magnetometers. Using these sensors, the system may be capable of automatically enabling and switching between camera systems depending on the position of the surgeon's head. For example, when the surgeon looks down, the system may enable the front-facing cameras 5, and then when the surgeon looks up or straight ahead, the system may enable the downward cameras 5 to permit the surgeon to comfortably find a forward-looking position while the downward facing cameras 5 capture the surgeon's hands and the operating space. Upon a voice command issued from the surgeon, the system may switch off the RR cameras 5 and convert to projecting the images from a scope or digital microscope.

The accurate alignment of AXR images with RR images may be achieved by using AI and a set of trackers 6, which may be used to determine the exact position of the cameras 5 and the patient's body. The AI engine together trackers 6 may identify and track fiducial markers placed on the surface of specific structures that remain still during surgery, such as iliac crest, clavicles, etc., and thus provide the system with points of reference. The system may take the fiducial marker information and fuse it with other inertial measurement data, which may be provided by the internal array of inertial measurement units 7, to provide a stable localization of the overlay system. The system may utilize proprietary 2D/3D software maximized for surgery.

The system may include a six degrees of freedom (6DoF) sub-system capable of providing real-time interfacing and no time loss between accessing 3D-type CT or MRI scans and projecting those images for surgery.

The system may be capable of displaying CG images over the top of pass-through RR. This may include presenting images generated using a fusion of optical images with near-infrared fluorescence images not visible to the human eye. These images can provide more useful immediate feedback that is overlayed in context to what is needed, such as blood flow. This technique may be used to increase precision by providing additional data for the surgeon to consider. Using this technique, surgeons could be able to detect blood vessels under the organ surface or detect other tissue abnormalities.

The system may be used as a digital magnifier, providing up to 10× magnification.

The AXR surgical system may further comprise one or more microphones in communication with the central processing unit, where the system is capable of being controlled via voice input via the microphone, input from the eye-tracking subsystem, or a combination of voice input via the microphone and input from the eye-tracking subsystem. The one or more microphones may be configured to create noise cancellation, or the AXR headset may include noise cancelling microphones to reduce, eliminate, or remove background noise so that the receiving person, device, or AXR headset itself can better understand the speech of the user. The wearable device may further comprise a battery and a remote communication device such that the wearable device is wireless and has communication features. The AXR headset may contain one or more batteries. In the case of more than one battery, the primary battery may be located in an external position on the headset in a manner to facilitate removal and replacement of the battery during use. The primary battery may include a mechanism for a spring-loaded battery to facilitate removal during use. In case of primary battery exhaustion, a surgery tech may press the spring-loaded battery in the back of the headset, then reattach a new, fully charged battery. The AXR headset in this instance may include a hot-swap feature, which may include one or more secondar, typically smaller, batteries, which typically would only carry enough capacity to last a few minutes. Thus, when the primary battery is exhausted, the common battery control circuit may shift to the auxiliary battery to keep the headset functioning with all features continuing until the primary battery is replaced. The system may include a battery full/battery empty capacity feature which alerts the user and others that there is only a certain about of battery charge remaining so that a timely battery change may be planned.

As noted above, the system may be in communication with one or more second systems such that one or more remote users can view the images from the system on the one or more second systems and communicate will the user and other remote users. By utilizing gesturing recognition and other mentioned technologies embedded in all user's headsets, any number of wired or wireless connected, or networked users may see the same virtual image. Then, any connected user can point to a specific point or set of points, or define one or more areas in virtual space, on the commonly seen virtual image in all the user's AXR headsets, which may then communicate and correspond that same reference information into the view of a select set or all other user's AXR headsets or to any other monitors and displays in the network. This technique may work with either a current simultaneous view or a current or past picture or video feed. Since the controller on all connected and simultaneously viewing headsets knows exactly where each pixel exists in the displayed virtual image, it may be able to identify the specific point or set of points, or area or areas, of interest and transmit that information wirelessly, or over a wired connection, to create a corresponding marker on all connected user's headsets so that all connected users can see and understand the specific point, set of points, area, or areas of interest originated by the initial pointing user. Likewise, the point or set of points or area or areas commonly displayed may be used as a point of reference or a measurement. In addition to images, any textual, graphical, or other information may also be commonly viewed by connected users. In addition, any connected AXR headset user using the technologies mentioned herein or through AI techniques may choose to view commonly displayed 2D or 3D images or 2D or 3D models in the same perspective as another; or any user may choose a different perspective of the same 2D or 3D images or models.

Using AI techniques embedded in the AXR headset or in a repository or neural network in communication with the one or more AXR headsets, through wired, wireless, or over 5G Edge Computing connections, one or more current or stored images can be analyzed and compared against a data model or composite of data models to find either specific or general information based on specific criteria, and show a result as a virtual image(s) on one AXR headset in real-time or on a plurality of connected AXR headsets Alternatively, the AI engine may make a similar comparison with a number of specific criteria's or no criteria at all, and bring novel information inferred from the system.

Using these technologies, for instance, a 3D MRI virtual image of an organ could be managed or compared with AI by one of the techniques set out herein in virtual space by the surgeon without getting contaminated by touching a real object, in order to change the registry and orientation of the virtual organ image to match the RR organ to increase the surgeon's understanding of where to incise, inject, or perform some other similar surgical act. In the case of the manipulation of a virtual image to match a real image, as stated above, the system may increase or decrease the opacity gradient of the lenses, so that both the virtual organ and the real organ may be viewed, or aligned, by the surgeon seeing them both at the same time.

The wearable device 1 may be lightweight and may be wireless. One of the ways to reduce weight is to have only the cameras, a battery, and sensors in the headset 1 with connectors to a WI Gig modem using the fastest wireless protocol available, such as the IEEE 802.(a,y) protocol. Another embodiment places the intelligence in the headset 1, such as a Qualcomm XR-2 chipset, and have the chipset circuit board be connected to WI Gig modems to send/receive streaming video to/from another WI Gig connected location, such as a digital microscope, endoscope, or other surgery imaging device. In the case where the AXR headset receives video feed from such a surgery system, either a wire or wireless connection can be made. While WIFI IEEE 802.11 would work, the best method would be to use a WI Gig 802.11(ad;ay, ax) so that uncompressed video can be sent from any image producing system to the AXR headset. In addition, the AXR headset may include a 5G modem to be capable of edge computing at super-fast speeds. Edge Computing is a technique to bring data back from the cloud to a localized network where all computing goes to an on-site or close-by data center.

While the instant invention focuses on the medical applications, the same technology may be used in other sectors, where a user needs to have a primary view and the ability to have other reference views available. Further, where this invention states words like "surgeon" or "assistant" or "tech" this is used in the common context of surgery application, but the same function and features apply to anyone wearing the AXR headset.

Whereas, the devices and methods have been described in relation to the drawings and claims, it should be understood that other and further modifications, apart from those shown or suggested herein, may be made within the spirit and scope of this invention.

What is claimed is:

1. An AXR surgical system comprising:
   a wearable device comprising:
      one or more micro-displays;
      one or more lenses, where the micro-displays are capable of projecting images onto the lenses;
      a head-tracking subsystem; and
      an eye-tracking subsystem; and
   a central processing unit in communication with and capable of controlling the micro-displays, lenses, head-tracking subsystem, and eye-tracking subsystem;
where the system is capable of displaying images on the lenses with a position based on a user's head position as tracked by the head-tracking subsystem and the user's eye position as tracked by the eye-tracking subsystem, while allowing the user to see through the lenses where the images are not being projected; and
where the lenses comprise:
  a reflective layer; and
  a layer of cholesteric liquid crystal comprising a plurality of pixels where each pixel is capable of independently becoming opaque,
where the system is capable of selectively making pixels opaque only where images are projected by the micro-displays, while any pixels located where the images are not projected remain see-through.

2. The AXR surgical system of claim 1 where the camera lenses are capable of capturing a wider field of vision than the micro-displays are capable of projecting a reduced field of vision depending on the user's eye position.

3. The AXR surgical system of claim 1 where the wearable device further comprises one or more forward-facing cameras and where the images projected by the micro-displays are at least partially images obtained from the forward-facing cameras.

4. The AXR surgical system of claim 1 further comprising one or more microphones in communication with the central processing unit, where the system is capable of being controlled via voice input via the microphones, input from the eye-tracking subsystem, or a combination of voice input via the microphones and input from the eye-tracking subsystem.

5. The AXR surgical system of claim 4 where the microphones have noise cancelling features capable of reducing ambient noise.

6. The AXR surgical system of claim 1 where the wearable device further comprises one or more batteries and a hot-swap feature.

7. The AXR surgical system of claim 6 where the wearable device further comprises a remote communication device such that the wearable device is wireless.

8. The AXR surgical system of claim 1 where the system is in communication with one or more second systems such that one or more remote users can view the images from any system on the one or more second systems and communicate with the user and other remote users.

9. The AXR surgical system of claim 1 where the images projected by the micro-displays are from preoperative imaging and where the system is capable of aligning the images with a patient.

10. The AXR surgical system of claim 1 where the system is in communication with one or more second systems such that one or more remote users can view images from an originating system on the one or more second systems in the same or different perspective as exists on the originating system and communicate with the user and other remote users.

11. The AXR surgical system of claim 1 where the system is in communication with one or more second systems such that one or more remote users can view the images from a system on the one or more second systems and analyze the images with AI technologies the result of which would be visible to all users.

12. The AXR surgical system of claim 1 further comprising at least one collimator located between the micro-displays and the reflective layer such that the at least one collimator is capable of concentrating rays from the micro-displays in an eye box while utilizing less resolution in a periphery.

13. The AXR surgical system of claim 1 where the wearable device further comprises one or more at least partially downward-facing cameras and where the images projected by the micro-displays are at least partially images obtained from the at least partially downward-facing cameras.

14. The AXR surgical system of claim 1 further comprising a remote camera system in wireless communication with the wearable device, where the images come from the remote camera system.

15. The AXR surgical system of claim 14 where the remote camera system is mounted on a six-axis cobotic arm.

16. The AXR surgical system of claim 15 where the cobotic arm is in communication with the system such that the cobotic arm is controlled by the user.

17. The AXR surgical system of claim 1 where the system is capable of centering an image in a field of view of the user and subsequently repositioning the image based on the user's eye position as tracked by the eye-tracking subsystem.

18. The AXR surgical system of claim 1 where the wearable device is wireless and is synced with one or more wired display systems such that the system is capable of presenting a simultaneous view on the wearable device and on the one or more wired display systems.

* * * * *